United States Patent [19]

McFall

[11] Patent Number: 5,561,855
[45] Date of Patent: Oct. 8, 1996

[54] VENTILATED WELDER'S HELMET

[76] Inventor: Mike G. McFall, 224 Rivercrest Dr., Sealy, Tex. 77474

[21] Appl. No.: 368,345

[22] Filed: Jan. 4, 1995

[51] Int. Cl.⁶ .................................................. A61F 9/06
[52] U.S. Cl. .................. 2/8; 2/171.3; 2/906; 250/208.6; 250/221
[58] Field of Search .................... 2/7, 8, 436, 171.3, 2/906; 250/208.6, 221, 222.1

[56] References Cited

U.S. PATENT DOCUMENTS

| | | |
|---|---|---|
| D. 308,416 | 6/1990 | Brumbach . |
| 3,238,535 | 3/1966 | Richey .............................................. 2/8 |
| 4,309,774 | 1/1982 | Guzowski . |
| 4,680,815 | 7/1987 | Hirsch et al. . |
| 4,893,356 | 1/1990 | Waters . |
| 4,899,039 | 2/1990 | Taylor et al. ......................... 250/208.6 |
| 5,029,342 | 7/1991 | Stein et al. ....................................... 2/8 |
| 5,031,237 | 7/1991 | Honrud . |
| 5,123,114 | 6/1992 | Desanti ............................................ 2/8 |

*Primary Examiner*—Michael A. Neas
*Attorney, Agent, or Firm*—Stephen R. Greiner

[57] ABSTRACT

A welder's helmet having a plurality of photovoltaic cell panels, responsive to light produced during welding operations, for driving a pair of fans secured to opposing side walls of a head protecting shell. The photovoltaic cell panels are angularly mounted to the shell beneath a viewing window provided therein so as to permit the head of the wearer to be turned away from the welding area without affecting fan output. During operation, each of the paired fans impels air through an opening in the shell into the interior space defined by the shell. An optional battery pack, electrically connected to the fan motors provides an electrical power back-up for energizing the fans in the event that insufficient light is available to the photovoltaic panels.

17 Claims, 1 Drawing Sheet

VENTILATED WELDER'S HELMET

FIELD OF THE INVENTION

The present invention relates generally to articles of apparel and, more particularly, to a head covering having forced air circulating means.

BACKGROUND OF THE INVENTION

To protect the head of an individual conducting welding operations, a helmet is usually employed. Such helmets typically include a rigid shell adapted to, at least, partially enclose the head of a wearer to defend it from incandescent matter ejected from a welding area. A darkened window in the front surface of the shell permits the wearer to observe the welding area while shielding the eyes from the high-intensity light emitted by a welding heat source such as an electric arc or acetylene torch flame. As air circulation through most welding helmets is limited, excessive perspiration and rapid fatigue can occur as the helmet wearer's head and body are warmed by energy radiated from the welding heat source.

Welding helmets have been proposed which provide automatic ventilation to a wearer through the use of a fan powered by photovoltaic or solar cells. Unfortunately, the proposed helmets are relatively complex, expensive and difficult to manufacture. Further, such helmets have heretofore included only a single, planar, solar cell panel on the exterior surface thereof for receiving light from a source like an electric arc or gas flame.

In order to power the fan, a wearer of one of the previously proposed helmets is required to continuously maintain his or her head in a fixed orientation wherein the single solar cell panel more-or-less directly faces the light source. In the frequent situations where the head of a wearer must turn away from the light source, ventilation provided by the fan is undesirably reduced or abated altogether. There remains a need, then, for a welder's helmet which may be automatically ventilated by initiation of a light source, such as an electric arc, and which will remain consistently ventilated when the head of the helmet wearer is turned to the left or right relative to the light source.

SUMMARY OF THE INVENTION

In light of the foregoing need, it is a principal object of the invention to provide a welder's helmet with an array of one or more photovoltaic cell panels, responsive to the light generated by a welding operation, for driving a pair of fans on opposite sides of a head-protecting shell. When the welding arc or torch is struck, the light therefrom will impinge on the photovoltaic cell panels and generate sufficient electricity to drive the fans. As the photovoltaic panels are angularly mounted on the protective shell below the viewing window, the head of a wearer may be advantageously turned from side-to-side, as desired, without affecting the operation of the fans.

It is a further object of the invention to provide a helmet of the type described wherein each of the fans impels air from the exterior of the helmet into its interior space through separate openings on opposite sides of the protective shell. A pair of housings, each accommodating a single fan, define air flow chambers which direct air from an intake vent to the shell openings. A spark-arresting screen covers each air intake vent, preventing incandescent matter ejected from the welding area from reaching the head of a wearer and causing burns. As air is exhausted from the unsealed rear of the helmet, fresh air is continuously drawn in through each air flow chamber to cool the wearer.

It is a feature of this invention to have a manually adjustable rheostat operably connected between a photovoltaic cell array and an electric fan motor to control the electrical current flow to the motor and, therefore, control the fan speed. By simple adjustment of a rheostat knob extending outwardly from the helmet, the air stream generated in a particular welding circumstance may be precisely controlled.

Because welder's helmets are often used in smokey or highly confined environments, it is an additional object of the invention to provide a welder's helmet as described hereinabove with an external, remote battery pack and associated electrical cable as a back-up, electrical current source to power the fans in the event that light received by the photovoltaic cell panels from a welding area is insufficient to do so.

It is an object of the invention to provide improved elements and arrangements thereof in an ventilated welder's helmet for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
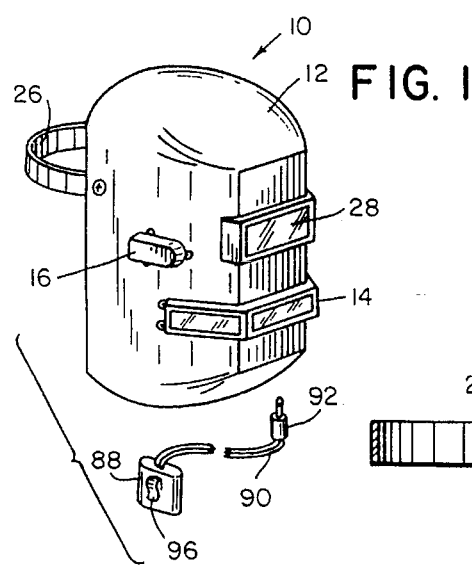
FIG. 1 is a perspective view of a ventilated welder's helmet and associated battery pack in accordance with the present invention.

Referring now to the drawings, and particularly to FIG. 1 thereof, there is shown a ventilated welder's helmet, designated generally as 10, in accordance with the present invention. The helmet 10 includes a protective shell 12 having means for forcing air into the space enclosed by the shell so as to cool the head of a wearer. A photovoltaic or solar cell array 14, responsive to the intense light generated by a welding operation, is secured to the front surface of the shell 12. When exposed to a light source, the array 14 drives a pair of small fans, each of which is positioned within a separate enclosure or housing 16 secured to opposing sides of the shell 12. Each housing 16 defines an air flow chamber through which fresh air may be drawn from the shell exterior and impelled toward opposite sides of the wearer's face and head, cooling the wearer in the process.

Although numerous, conventional, welding helmet designs may be adapted to incorporate the features of the instant invention, the preferred helmet shell 12 construction includes: a front wall 18, laterally-spaced side walls 20 extending rearwardly from the front wall, and longitudinally-spaced top and bottom walls 22 and 24 extending rearwardly from the front wall so as to connect the side walls together in an integral, bowl-like structure which protects the wearer's face and head in well-known fashion. The shell 12 may be constructed from any suitable, rigid material including, but not limited to, fiberglass, plastic or metal alloy. Head mounting straps 26 are secured to the top of the shell 12 for support of the helmet 10 by the head of a wearer. Beneath the straps 26, in the front wall 18, is provided a darkened, viewing window 28 through which the wearer may observe the welding area.

Figure 3:
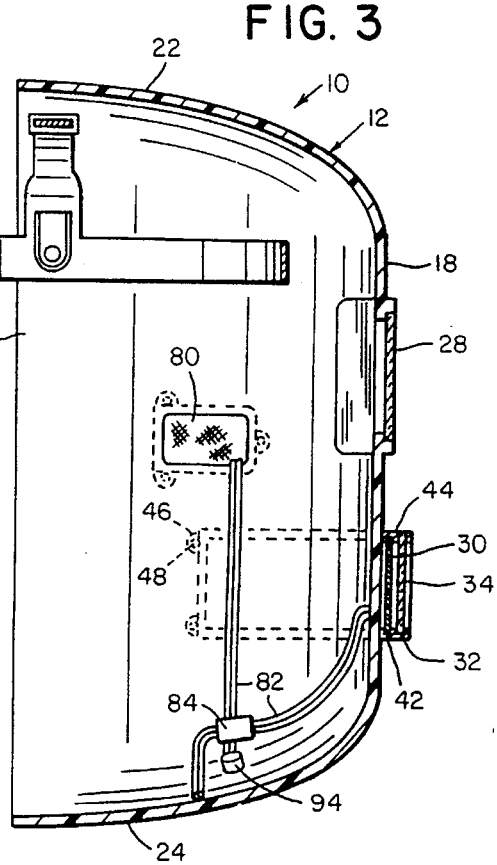
FIG. 3 is a cross-sectional view of the welder's helmet taken along line 3—3 of FIG. 2.
Figure 2:
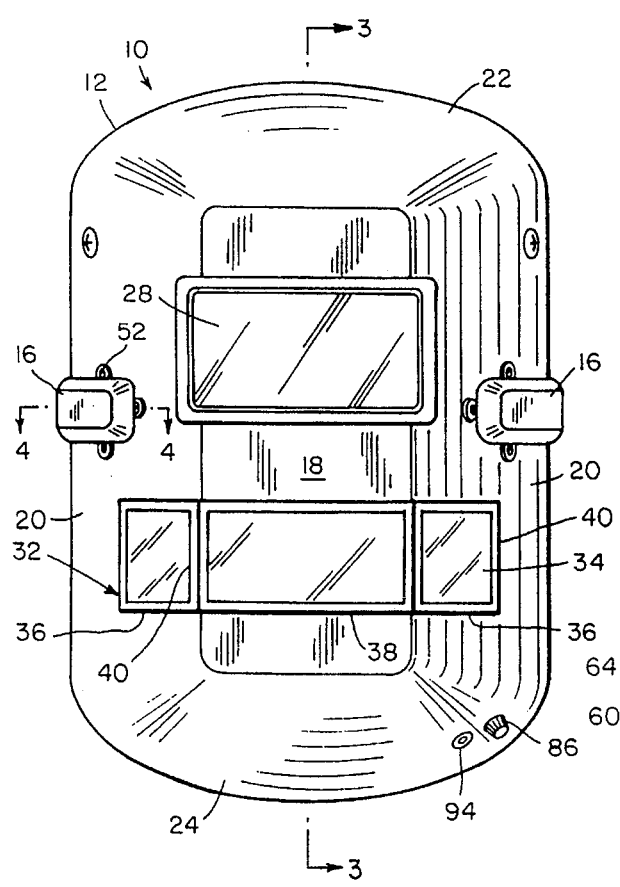
FIG. 2 is a front elevational view of the welder's helmet.

Mounted on the shell 12 beneath the viewing window 28 is the photovoltaic cell array 14 wherein a plurality of photovoltaic cell panels 30 are individually located within a supporting frame 32, each of said panels 30 being positioned behind a corresponding protective lens 34 of plastic or glass. As shown in FIGS. 2 and 3, the supporting frame 32 includes a horizontally disposed base member defined by a pair lateral legs 36 angularly joined together by a central leg 38. Preferably, the legs 36 and 38 are all of substantially equal length. At the opposing ends of the base member, and at the angled junctions between the lateral legs 36 and central leg 38, are vertical legs 40 extending upwardly therefrom. Side-by-side channels 42 in the legs 36, 38 and 40 permit the plurality of photovoltaic panels 30 and lens 34 to be slidably, yet snugly, located in the frame 32 for use. A plurality of photovoltaic cell retaining legs 44, fixedly secured by adhesive cement to the respective tops of adjacent vertical legs 40, permanently capture the photovoltaic cell panels 30 within the frame 32. Each protective lens 34, on the other hand, may be slipped vertically out of the frame 32 as desired by the application of a light force for cleaning or replacement. Bored flanges 46 extending from the outermost, vertical legs 40 permit the frame 32 to be secured to the shell 12 by conventional threaded fasteners 48.

As best seen in FIG. 1, the frame 32 conforms to the angular, front surface of the helmet shell 12. Each photovoltaic cell panel 30, being rigid and substantially planar in form, then, is positioned by the frame 32 closely adjacent, and parallel to, the front wall 18 or one of the laterally-positioned side walls 20 so as to offer the maximum freedom of movement in confined welding areas. As the side walls 20 meet the front wall 18 of the shell 12 at a preferred, interior angle ranging from 135 to 150 degrees, the helmet wearer is free to turn his or her head from side-to-side to avoid obstacles and still receive ample light energy from the welding area to drive the fans.

Figure 4:
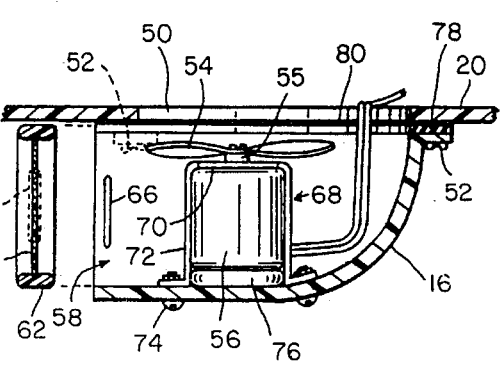
FIG. 4 is a partial cross-sectional view taken along line 4—4 of FIG. 2 illustrating fan housing details.

Covering a small opening 50 formed in each of the side walls 20 is a scoop-shaped housing 16 secured to the shell 12 by conventional, threaded fasteners 52. As shown in FIG. 4, within each housing 16 is mounted an electrically driven fan comprising a fan blade 54 carried by drive shaft 55 extending from DC motor 56. When rotated by the motor shaft 55, the fan blade 54 draws air through a rearwardly-facing, inlet vent 58, defined by the housing 16 and adjacent side wall 20, into the housing 16, and discharges the air through the opening 50 provided in the side wall 20 toward the wearer.

Preferably, the inlet vent 58 is positioned approximately midway between the forward and rearward edges of the side wall 20. This positioning of the inlet vent 58 is one which is remote from the front wall 18 so that air moved through the housing 16 by the fan will contain little, if any, of the noxious fumes produced during welding operations. The location of the inlet vent 58 is also remote from the rearward edge of the side wall 20 so that the air moving through the housing 16 will not include substantial volumes of stale, perspiration-laden air discharged from the rear of the helmet 10.

Covering the inlet vent 58 is a removable, spark-arresting screen 60. The screen 60, preferably fabricated from finely drawn wire, is supported about its periphery by a resilient frame 62. Outwardly projecting tabs 64, adapted for selective engagement in corresponding slots 66 in the housing 16, permit the frame 62 to be easily disengaged from the housing when desired. Although the frame 62 may be constructed in any suitable manner, it is contemplated that such could best be formed by heat-fusing two, like halves together about the screen 60 in well-known fashion.

The finely drawn wire comprising the screen 60 is preferably formed of copper or a copper alloy such as brass. Not only are such materials fireproof, but they have a tendency to retain, adhered to their respective surfaces, incandescent particles of high-temperature slag, often randomly ejected from a welding area, as they cool. Thus, because the heated slag particles tend to adhere to, and become captured by, the copper or copper alloy screen 60, they are prevented from being deflected onto the wearer's clothing or elsewhere where such could ignite a fire. Of course, the preferred screen 60 has a mesh sufficiently fine so as to prevent the passage of slag particles, greatly diminishing the risk of burns to the head of a wearer of the instant helmet.

With continuing reference to FIG. 4, the driving motor 56 may be seen to be fixedly secured within the housing 16 by a harness 68. Preferably, the harness 68 includes a ring 70 adapted to snugly engage one end of the motor 56 and permit unimpeded rotation of the motor shaft 55 passing through the open center thereof. A pair of generally L-shaped brackets 72 extend normally from opposite sides of the ring 70 and are attached by conventional threaded fasteners 74 to the housing 16. Clamped between the motor 56 and housing 16 is a relatively thin, rubber disk 76 for dampening any vibrations emitted by the motor 56 during its operation. Additional vibration dampening is provided by a gasket 78 of heat-resistant material which fixedly clamps a protective screen 80 over opening 50 between the housing 16 and side wall 20.

Each driving motor 56 is electrically connected through electrical conductors 82 to the photovoltaic cell panels 30. As stated hereinabove, these photovoltaic cell panels 30 are sensitive to light and, upon receiving light energy at a satisfactory level, will cause operation of each motor 56. Connected in electrical series with the motors 56 and photovoltaic cell panels 30, by means of conductors 82, is a manually-operable rheostat 84. By rotating the rheostat adjustment knob 86 projecting from the bottom wall 24, the wearer of the helmet 10 may vary the amount of electrical current delivered to the motors 56, thus, permitting the speed of the motors 56 to be regulated as desired. When the knob 86 is rotated to its "off" setting, the flow of electrical current to the motors 56 is fully abated thereby preventing the motors from continually operating when not required.

The helmet 10 is provided with alternative means for supplying electrical current to the motors 56 when lighting conditions in a given welding area are inadequate to power the fans through operation of the photovoltaic cell panels 30. Preferably, such means include a battery pack comprising at least one rechargeable storage battery 88 operably connected to the motors 56 through an electrical power cable 90. As illustrated, a plug 92, provided at the free end of the power cable 90, may be placed in electrical communication with the motors 56, by its insertion into an appropriate socket 94 in the bottom wall 24. A spring clip 96 secured to the storage battery 88 permits convenient attachment thereof to the belt or other garment of the helmet wearer.

From the foregoing, it is believed that the operation of the helmet 10 should be readily apparent to one of ordinary skill in the art. Once a welding arc or the like is initiated, such may be safely viewed through the window 28 by the helmet wearer. The photovoltaic cell panels 30 respond to the light emanating from the arc by producing electricity which operates the DC motors 56 thereby causing the rotation of the fan blades 54. Air impelled through each of the housings 16 against the sides of the wearer's face and head by the fan blades 54 causes perspiration on the skin to evaporate. As evaporation continues, such cools not only the surface of the skin but also the blood that courses through it thereby cooling the entire body of the wearer.

Because of the angular mounting of the photovoltaic panels 30 upon protective shell 12, the helmet wearer is free to turn his or her head from side-to-side during welding operations and yet receive constant cooling from the fans. Fan speed may be varied if desired, however, by manual adjustment of the rheostat knob 86. Upon terminating the welding operation, the motors 56 are automatically deactivated to be again be reactivated upon initiation of another welding operation. If a particular welding operation delivers minimal light to the photovoltaic cell panels 30, an electrical current may be drawn from the storage battery 88 to power the fans.

While the inventive helmet has been described with a high degree of particularity, it will be appreciated by those skilled in the art that numerous modifications and substitutions may be made thereto. For example, while the preferred location of the photovoltaic cell array 14 is beneath the viewing window 28, for closer positioning to most welding operations, the array 14 could be located above the window 28 for optimizing the helmet's weight distribution. Additionally, substituted for the photovoltaic cell retaining frame 32 described hereinabove may be a similar, but substantially planar structure, formed from a flexible material which may be appropriately bent upon its installation to conform to the angularly-joined wall surfaces of the shell 12. Therefore, it is to be understood that the present invention is not limited to the exemplary embodiment described above, but encompasses any and all embodiments within the scope of the following claims.

I claim:

1. A welder's helmet, comprising:

a protective shell having a front wall and a pair of laterally-spaced side walls extending rearwardly from said front wall so as to define an interior space adapted to receive the head of a wearer;

an electric motor secured to said protective shell;

a fan blade rotatable by said electric motor for impelling air into said interior space; and, a plurality of photovoltaic cell panels in electrical communication with said electric motor, said plurality of photovoltaic cell panels mounted upon said protective shell wherein at least one of said plurality of photovoltaic panels is positioned adjacent said front wall and each of said pair of laterally-spaced side walls.

2. The welder's helmet according to claim 1 wherein said plurality of photovoltaic panels are mounted side-by-side upon said protective shell.

3. The welder's helmet according to claim 1 further comprising:

a housing attached to said protective shell for directing air impelled by said fan blade through an opening in said protective shell into said interior space, said housing defining an air flow chamber having an air intake vent and an air exhaust vent adjacent said opening; and, a screen covering said air intake vent.

4. The welder's helmet according to claim 3 wherein said electric motor and fan blade are located within said air flow chamber.

5. The welder's helmet according to claim 3 wherein said screen comprises a spark-arresting material.

6. The welder's helmet according to claim 1 further comprising a storage battery in selective electrical communication with said motor.

7. The welder's helmet according to claim 1 wherein a rheostat is electrically connected between said plurality of photovoltaic cell panels and said electric motor for controlling motor speed.

8. A welder's helmet, comprising:

a protective shell defining an interior space adapted to receive the head of a wearer;

a viewing window, oriented in a first plane, in said protective shell;

an electric motor secured to said protective shell;

a fan blade rotatable by said electric motor for impelling air into said interior space; and, a plurality of photovoltaic panels, in electrical communication with said electric motor, mounted side-by-side upon said shell adjacent said viewing window, one of said plurality of photovoltaic panels being positioned in a second plane substantially parallel to said first plane, and another one of said plurality of photovoltaic panels being positioned in a third plane, said second plane and said third plane intersecting at an angle.

9. The welder's helmet according to claim 8 further comprising:

a housing attached to said protective shell for directing air impelled by said fan blade through an opening in said protective shell into said interior space, said housing defining an air flow chamber having an air intake vent and an air exhaust vent adjacent said opening; and, a spark-arresting screen covering said air intake vent.

10. The welder's helmet according to claim 9 wherein said electric motor and said fan blade are located within said air flow chamber.

11. The welder's helmet according to claim 8 wherein a rheostat is electrically connected between said first photovoltaic panel and said motor for controlling motor speed.

12. A ventilated welder's helmet, comprising:

a protective shell having a front wall and a pair of laterally-spaced side walls extending rearwardly from said front wall so as to define an interior space adapted to receive the head of a wearer;

a viewing window in said front wall;

a pair of electric motors secured to said protective shell;

a fan blade rotatable by each said electric motor for impelling air into said interior space; and, a plurality of photovoltaic panels in electrical communication with said motors, said plurality of photovoltaic panels mounted upon said protective shell wherein at least one of said plurality of photovoltaic panels is positioned adjacent said front wall and each of said pair of laterally-spaced side walls.

13. The ventilated welder's helmet according to claim 12 further comprising a housing attached to each of said side walls for directing air impelled by said fan blade through an opening in each said side wall into said interior space, each said housing defining an air flow chamber having an air intake vent and an air exhaust vent adjacent said opening.

14. The ventilated welder's helmet according to claim 13 further comprising a spark-arresting screen covering each said air intake vent.

15. The ventilated welder's helmet according to claim 13 wherein one of said pair of electric motors and its carried fan blade is located within each said air flow chamber.

16. The ventilated welder's helmet according to claim 13 wherein each said side wall includes a forward and a rearward edge and each said air intake vent is positioned substantially midway between said forward edge and said rearward edge.

17. The ventilated welder's helmet according to claim 12 further comprising a storage battery in selective electrical communication with said motor.

\* \* \* \* \*